(12) United States Patent
Miller et al.

(10) Patent No.: US 9,575,165 B2
(45) Date of Patent: Feb. 21, 2017

(54) ULTRASOUND PROBE AND ULTRASOUND IMAGING SYSTEM

(75) Inventors: Steven Charles Miller, Phoenix, AZ (US); Kjell Kristoffersen, Horten (NO); Bruno Hans Haider, Niskayuna, NY (US)

(73) Assignee: General Electric Company, Schenectady, NY (US)

(*) Notice: Subject to any disclaimer, the term of this patent is extended or adjusted under 35 U.S.C. 154(b) by 595 days.

(21) Appl. No.: 12/786,950

(22) Filed: May 25, 2010

(65) Prior Publication Data

US 2011/0295119 A1    Dec. 1, 2011

(51) Int. Cl.
| | |
|---|---|
| *A61B 8/00* | (2006.01) |
| *G01S 7/52* | (2006.01) |
| *A61B 8/08* | (2006.01) |
| *G01S 15/89* | (2006.01) |
| *G10K 11/34* | (2006.01) |

(52) U.S. Cl.
CPC ........... *G01S 7/5208* (2013.01); *A61B 8/4488* (2013.01); *A61B 8/488* (2013.01); *G01S 7/52084* (2013.01); *G01S 15/8925* (2013.01); *G01S 15/8927* (2013.01); *G10K 11/345* (2013.01); *G01S 7/5203* (2013.01); *G01S 15/8913* (2013.01); *G01S 15/8915* (2013.01)

(58) Field of Classification Search
CPC ........... A61B 8/08; A61B 8/00; A61B 8/4488; A61B 8/488
USPC ....... 600/407, 413, 437, 441, 443, 445, 446, 600/447, 459; 327/2, 105, 108, 141, 161, 327/163
See application file for complete search history.

(56) References Cited

U.S. PATENT DOCUMENTS

| | | | | |
|---|---|---|---|---|
| 5,951,479 A | * | 9/1999 | Holm et al. | 600/447 |
| 6,013,032 A | * | 1/2000 | Savord | 600/443 |
| 6,106,472 A | * | 8/2000 | Chiang et al. | 600/447 |
| 6,856,175 B2 | * | 2/2005 | Wodnicki | 327/108 |
| 7,029,445 B2 | * | 4/2006 | Shinomura et al. | 600/443 |
| 7,217,243 B2 | * | 5/2007 | Takeuchi | 600/447 |

(Continued)

FOREIGN PATENT DOCUMENTS

| | | |
|---|---|---|
| CN | 1189217 A | 7/1998 |
| JP | 09299361 A | 11/1997 |

(Continued)

OTHER PUBLICATIONS

Unofficial English translation of Office Action and Search Report issued in connection with corresponding CN Application No. 201110151969.5 on Mar. 4, 2014.

(Continued)

*Primary Examiner* — Joel Lamprecht
(74) *Attorney, Agent, or Firm* — John D. Russell; B. Anna McCoy (57) ABSTRACT

An ultrasound probe and an ultrasound imaging system include a plurality of transducer elements arranged in an array. The plurality of transducer elements are organized to form a transmit aperture and a receive aperture. The ultrasound probe and ultrasound imaging system include a plurality of summing nodes. The ultrasound probe and ultrasound imaging system include a set of receive switches associated with each of the transducer elements in the receive aperture. Each set of receive switches is configured to selectively connect the associated transducer element to any one of the plurality of summing nodes.

23 Claims, 6 Drawing Sheets

(56) References Cited

U.S. PATENT DOCUMENTS

| | | | |
|---|---|---|---|
| 7,280,435 B2 * | 10/2007 | Thomenius et al. | 367/153 |
| 7,307,374 B2 * | 12/2007 | Ossmann | 310/335 |
| 8,128,565 B2 | 3/2012 | Ohtake et al. | |
| 2005/0203391 A1 * | 9/2005 | Phelps et al. | 600/437 |
| 2007/0167781 A1 * | 7/2007 | Vortman | G01S 15/8925 600/443 |
| 2009/0005684 A1 * | 1/2009 | Kristoffersen et al. | 600/447 |
| 2009/0306510 A1 | 12/2009 | Hashiba et al. | |

FOREIGN PATENT DOCUMENTS

| | | | |
|---|---|---|---|
| JP | 2001170052 A | 6/2001 | |
| JP | 2005034634 A | 2/2005 | |
| JP | 2005278918 A | 10/2005 | |
| JP | 2005342194 A | 12/2005 | |
| JP | 2006061693 A | 3/2006 | |
| JP | 2006223612 A | 8/2006 | |
| JP | 2008518553 A | 5/2008 | |
| JP | 2009006141 A | 1/2009 | |

OTHER PUBLICATIONS

Unofficial English translation of Office Action issued in connection with corresponding JP Application No. 2011-109960 on Nov. 4, 2015.

Unofficial English translation of the Chinese Office Action issued in connection with corresponding CN Application No. 201110151969.5 on Sep. 17, 2014.

* cited by examiner

ULTRASOUND PROBE AND ULTRASOUND IMAGING SYSTEM

FIELD OF THE INVENTION

This disclosure relates generally to ultrasound imaging and specifically to an ultrasound probe and an ultrasound imaging system with a plurality of summing nodes and/or a plurality of distribution nodes connected to the transducer elements in the ultrasound probe.

BACKGROUND OF THE INVENTION

A conventional ultrasound imaging system comprises an array of ultrasonic transducer elements for transmitting an ultrasound beam and receiving a reflected beam from the object being studied. By selecting the time delay (or phase) and amplitude of the applied voltages, the individual transducer elements can be controlled to produce ultrasonic waves which combine to form a net ultrasonic wave that travels along a preferred vector direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the phase rotation and amplitude of the applied voltages, the beam with its focal point can be moved in a plane to scan the object.

The same principles apply when the transducer array is employed to receive the reflected sound energy. The voltages produced at the receiving elements are summed so that the net signal is indicative of the ultrasound reflected from a single focal point in the object. As with the transmission mode, this focused reception of the ultrasonic energy is achieved by imparting a separate phase and gain to the signal from each receiving element.

Many conventional ultrasound imaging systems have included a two-dimensional transducer array (hereinafter a 2D transducer array). For purposes of this disclosure, a 2D transducer array is defined to include a transducer array where the center points of the transducer elements form a two-dimensional pattern. The two-dimensional pattern may follow a curved surface according to some embodiments. Typically, the transducer elements are dimensionally similar in both length and width in a 2D transducer array. Also, a 2D transducer array may have full electronic focusing and steering. The 2D transducer array typically comprises a number of transducer elements arranged in a grid; the grid may have a square, rectangular, hexagonal, or other basis. By controlling the timing and amplitude of the elements in the 2D transducer array, it is possible to steer the transmitted ultrasound beam simultaneously in both an azimuth direction and in an elevation direction. The use of a 2D transducer array allows the ultrasound transducer or probe to have greater flexibility.

It is often advantageous to collect ultrasound data using a continuous-wave Doppler imaging mode for the imaging of moving fluids such as blood. In a continuous-wave Doppler imaging mode, a group of transducer elements in a transmit aperture are used to transmit ultrasonic energy into the anatomical region being imaged. A second group of transducer elements in a separate receive aperture are used to detect reflected ultrasonic energy that is reflected back from the region being imaged. Typically, for a probe with a 1D transducer array, there is an amplifier associated with each of the transducer elements in the receive aperture. However, due to both space and power constraints, the amplifiers within a probe with a 2D transducer array typically have limited dynamic range, leaving them poorly-suited for procedures such as continuous-wave Doppler imaging. In continuous-wave Doppler imaging, the signals from moving blood may be orders of magnitude weaker than the signals from stationary tissue. For proper signal analysis, both the weak blood echoes and the strong tissue echoes must be processed. Using amplifiers with limited dynamic range, such those which would be found in a conventional probe with a 2D transducer array, to process the signals received during a continuous-wave Doppler acquisition may be problematic since the blood echo signals are so much smaller than the signals received from tissue. Generally, the use of amplifiers with a limited dynamic range for continuous-wave Doppler imaging will result in sub-optimal analysis of the blood echoes.

Additionally, 2D transducer arrays typically require electronic beamforming in close proximity to the transducer array for optimal results. However, conventional 2D arrays may have several thousand elements and it is not practical to bring electrical signals from all of these elements back to the ultrasound console for electronic beamforming.

For these and other reasons there is a need for a new ultrasound probe and a new ultrasound imaging system.

BRIEF DESCRIPTION OF THE INVENTION

The above-mentioned shortcomings, disadvantages and problems are addressed herein which will be understood by reading and understanding the following specification.

In an embodiment, an ultrasound probe includes a plurality of transducer elements arranged in an array. The plurality of transducer elements are organized to form a transmit aperture and a receive aperture. The ultrasound probe includes a plurality of summing nodes. The ultrasound probe also includes a plurality of sets of receive switches. Each set of receive switches is associated with a different one of the plurality of transducer elements in the receive aperture. Each set of receive switches is configured to selectively connect the associated transducer element to any one of the plurality of summing nodes.

In another embodiment, an ultrasound probe includes a plurality of transducer elements arranged in an array. The plurality of transducer elements are organized to form a transmit aperture and a receive aperture. The ultrasound probe includes a plurality of distribution nodes. The ultrasound probe includes a plurality of sets of transmit switches. Each set of transmit switches is associated with a different one of the plurality of transducer elements in the transmit aperture. Each set of the transmit switches is configured to selectively connect the associated transducer element to any one of the plurality of distribution nodes.

In another embodiment, an ultrasound imaging system includes a user interface and an ultrasound probe. The ultrasound probe includes a plurality of transducer elements arranged in an array. The plurality of transducer elements are organized to form a transmit aperture and a receive aperture. The ultrasound probe includes a plurality of summing nodes. The ultrasound probe includes a plurality of sets of receive switches. Each set of receive switches is associated with a different one of the transducer elements in the receive aperture. Each set of receive switches is configured to connect the associated transducer element to any one of the plurality of summing nodes. The ultrasound imaging system also includes a processor connected to the user interface and the ultrasound probe. The processor is configured to control the plurality of sets of receive switches in order to selectively connect a subset of the plurality of transducer elements in the receive aperture to one of the plurality of summing nodes.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
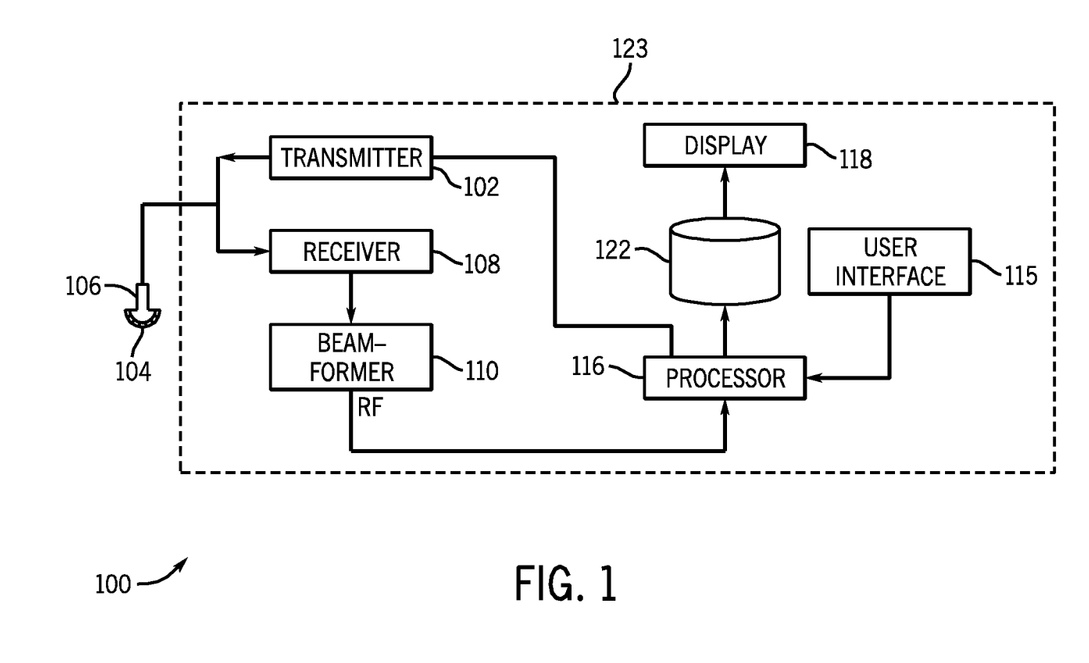
FIG. 1 is a schematic diagram of an ultrasound imaging system in accordance with an embodiment.

FIG. 1 is a schematic diagram of an ultrasound imaging system 100. The ultrasound imaging system 100 includes a transmitter 102 that drives transducer elements 104 within an ultrasound probe 106 to emit pulsed ultrasonic signals into a body (not shown). A variety of geometries may be used. The pulsed ultrasonic signals are back-scattered from structures in the body, like blood cells or muscular tissue, to produce echoes that return to the transducer elements 104. The echoes are converted into electrical signals, or ultrasound data, by the transducer elements 104 and the electrical signals are received by a receiver 108. For purposes of this disclosure, the term ultrasound data may include data that was acquired and/or processed by an ultrasound system. Additionally, the term ultrasound data is defined to include both RF ultrasound data and IQ ultrasound data, which will be discussed in detail hereinafter. The electrical signals representing the received echoes are passed through a beamformer 110 that outputs RF ultrasound data. RF ultrasound data may refer to data either before or after beamformation. A user interface 115 as described in more detail below may be used to control operation of the ultrasound system 100, including, to control the input of patient data, to change a scanning or display parameter, and the like.

The ultrasound imaging system 100 also includes a processor 116 to process the ultrasound data and prepare frames of ultrasound information for display on a display 118. The processor 116 is electrically connected to the transmitter 102. The processor 116 is indirectly connected to the probe 106 via the transmitter 102 and the beamformer 110. The processor 116 may control how the transducer elements 104 are used while scanning as will be described in more detail hereinafter. According to an embodiment, the processor 116 may also include a complex demodulator (not shown) that demodulates the RF ultrasound data and generates raw ultrasound data. For the purposes of this disclosure, the term "IQ ultrasound data" is defined to include demodulated ultrasound data that has not yet been processed for display as an image. The processor 116 is adapted to perform one or more processing operations according to a plurality of selectable ultrasound modalities on the ultrasound information. The ultrasound information may be processed in real-time during a scanning session as the echo signals are received. For the purposes of this disclosure, the term "real-time" is defined to include a procedure that is performed without any intentional delay. Additionally or alternatively, the ultrasound information may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire ultrasound information at a frame rate of, for example, 20 Hz to 30 Hz. However, other embodiments may acquire ultrasound information at a different rate. For example, some embodiments may acquire ultrasound information at a frame rate of over 100 Hz depending on the intended application. A memory 122 is included for storing processed frames of acquired ultrasound information that are not scheduled to be displayed immediately. In an exemplary embodiment, the memory 122 is of sufficient capacity to store at least several seconds worth of frames of ultrasound information. The frames of ultrasound information are stored in a manner to facilitate retrieval thereof according to its order or time of acquisition. The memory 122 may comprise any known data storage medium. An ultrasound console 123 includes all of the elements within the dashed line in FIG. 1. Other embodiments may include an ultrasound console with a slightly different combination of elements. However, according to this disclosure, the term "console" is defined to include at least a processor and a beamformer.

Optionally, embodiments of the present invention may be implemented utilizing contrast agents. Contrast imaging generates enhanced images of anatomical structures and blood flow in a body when using ultrasound contrast agents including microbubbles. After acquiring ultrasound data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, ultrasound information may be processed by other or different mode-related modules (e.g., B-mode, Color Doppler, power Doppler, M-mode, spectral Doppler anatomical M-mode, strain, strain rate, and the like) to form 2D or 3D data sets of image frames and the like. For example, one or more modules may generate B-mode, color Doppler, power Doppler, M-mode, anatomical M-mode, strain, strain rate, spectral Doppler image frames and combinations thereof, and the like. The image frames are stored along with timing information indicating a time at which the image frame was acquired in a memory. The modules may include, for example, a scan conversion module to perform scan conversion operations to convert the image frames from Polar to Cartesian coordinates. A video processor module may be provided that reads the image frames from a memory and displays the image frames in real time while a procedure is being carried out on a patient. A video processor module may store the image frames in an image memory, from which the images are read and displayed.

Figure 2:
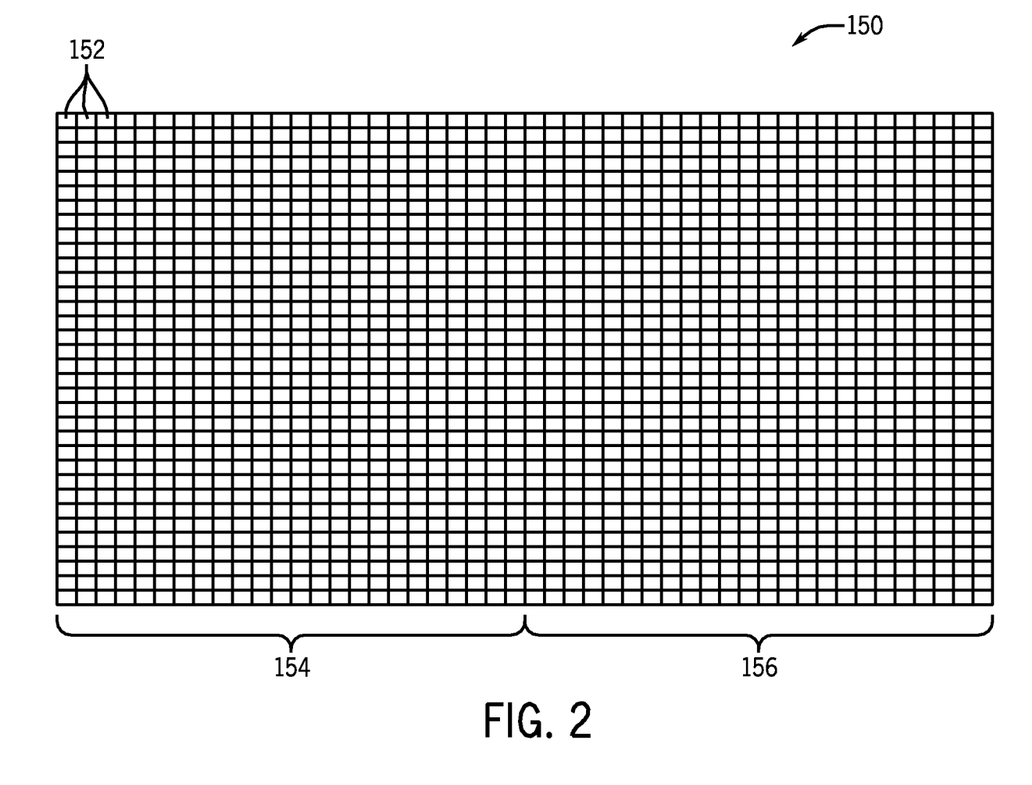
FIG. 2 is a schematic representation of a two-dimensional transducer array in accordance with an embodiment.

Referring to FIG. 2, a schematic representation of a two-dimensional (2D) transducer array is shown in accordance with an embodiment. The 2D transducer array 150 may be a component of a probe such as the ultrasound probe 106 shown in FIG. 1. The 2D transducer array 150 comprises a plurality of transducer elements 152 arranged into rows and columns. The embodiment shown in FIG. 2 has 35 rows and 48 columns, but other embodiments may have a different number of transducer elements and/or the transducer elements may be arranged differently. For example, an embodiment may have 7680 transducer elements arranged into 48 rows and 160 columns. For purposes of this disclosure, the azimuth direction will be defined to include an x-direction and the elevation direction will be defined to include a y-direction. The two-dimensional transducer array 150 may include a transmit aperture 154 and a receive aperture 156.

Figure 3:
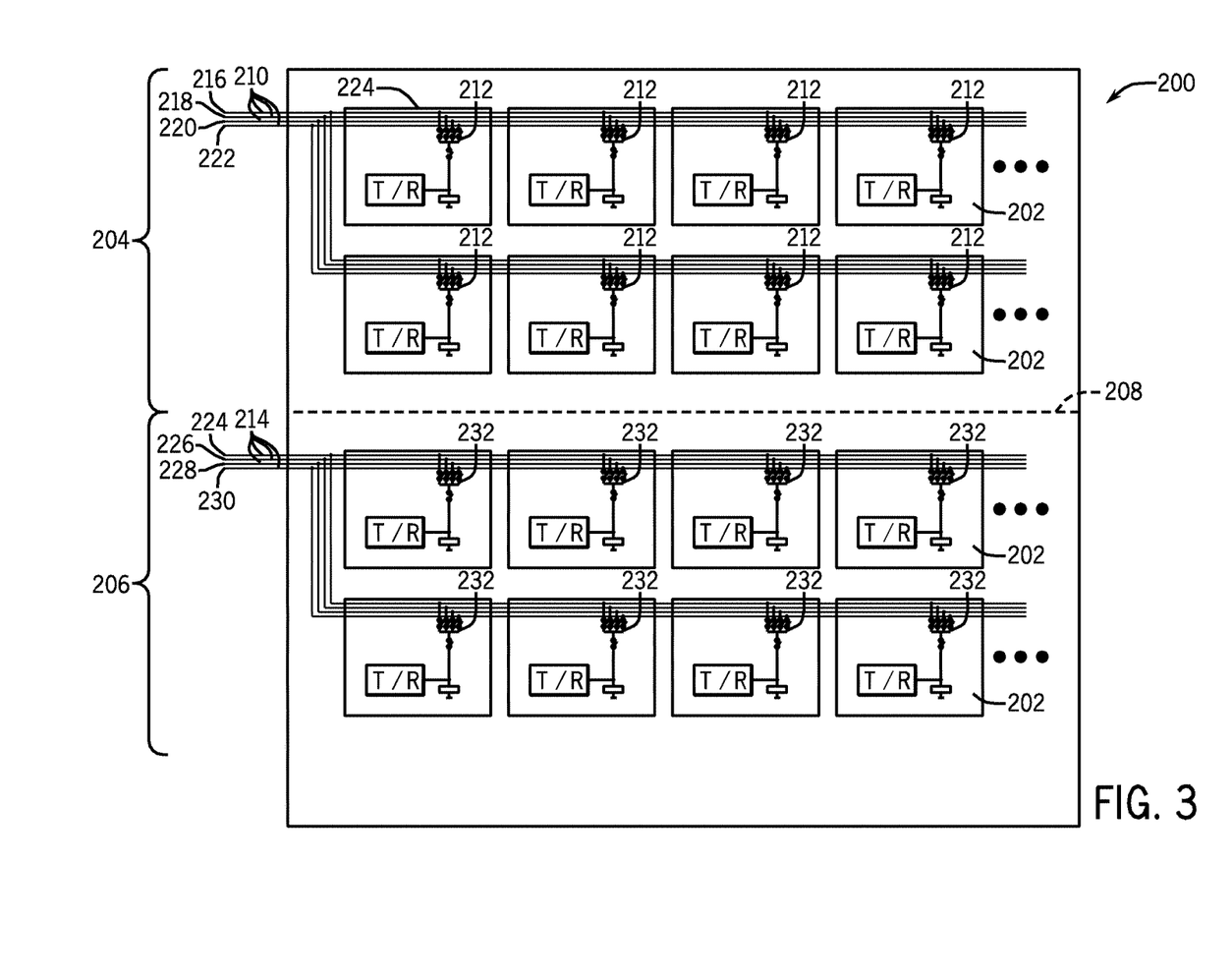
FIG. 3 is a schematic representation of a portion of an application-specific integrated circuit in accordance with an embodiment.

Referring to FIG. 3, a schematic representation of a portion of an application-specific integrated circuit, hereinafter ASIC, within an ultrasound probe is shown in accordance with an embodiment. The ASIC 200 may be positioned behind a transducer array, such as the 2D transducer array 150 shown in FIG. 2. The ASIC 200 includes a plurality of cells 202. According to an embodiment, each of the plurality of cells 202 within the ASIC 200 may be associated with a unique transducer element. For many operating modes, including continuous-wave Doppler mode, the transducer array 150 may be separated into a transmit aperture 154 (shown in FIG. 2) and a receiver aperture 156 (shown in FIG. 2) as was described previously. According to an embodiment, the plurality of cells 202 of the ASIC 200 are divided into a first plurality of cells 204 and a second plurality of cells 206. A dotted line 208 serves to separate the first plurality of cells 204 from the second plurality of cells 206. Each of the first plurality of cells 204 is associated with a transducer element in the transmit aperture 154 (Shown in FIG. 2) and each of the second plurality of cells 206 is associated with a transducer element in a receive aperture 156 (Shown in FIG. 2) according to an embodiment. Each of the cells 202 includes a set of switches that determines how the associated cell is connected to either one of a plurality of distribution nodes 210 or one of a plurality of summing nodes 214. For purposes of this disclosure, the term "associated" is defined to include being electrically connected. Additionally, with respect to the embodiment shown in FIG. 3, the term "associated" denotes that the configuration of the switches (either transmit switches or receive switches) on a particular cell is adapted to determine the routing of a signal either to or from a particular transducer element. Each of the elements within a cell, such as a set of transmit switches or a set of receive switches are, therefore, also associated with a single transducer element. Also, according to other embodiments, individual elements shown as within the ASIC 200 in FIG. 3 may be included in structures other than an ASIC. For clarity, only a small number of all the cells in ASIC 200 are represented in FIG. 3. As was described previously, according to an embodiment, there would be a unique cell in the ASIC for each transducer element 152 in the transducer array 150.

Referring to FIG. 2 and FIG. 3, according to an embodiment, each of the first plurality of cells 204 is selectively connectable to any one of the plurality of distribution nodes 210. The processor 116 (shown in FIG. 1) may be configured to control which subsets of the first plurality of cells 204, and therefore which of the transducer elements 152, are connected to each of the distribution nodes 210. The plurality of distribution nodes 210 are configured to carry transmission signals from the ultrasound console 123 (shown in FIG. 1) to the first plurality of cells 204 in the ASIC 200. The first plurality of cells 204 in turn carry the transmission signals to the transducer elements in the transmit aperture 154. All of the transducer elements connected to the same distribution node would receive a transmission signal from the transmitter 102 (shown in FIG. 1) with substantially the same phase. It is still possible for the processor 116 to effectively steer the ultrasound beam emitted from the transducer elements 152 by controlling which of the transducer elements 152 are connected to each of the distribution nodes 210 and by sending transmission signals with different phases through each of the distribution nodes 210. According to the embodiment shown in FIG. 3, the plurality of distribution nodes 210 includes four distribution nodes: a first distribution node 216, a second distribution node 218, a third distribution node 220 and a fourth distribution node 222. Other embodiments may include a different number of distribution nodes. Additional details about the sets of transmit switches 212 and the plurality of distribution nodes 210 will be described hereinafter.

Still referring to FIG. 3, each of the second plurality of cells 206 is selectively connectable to any one of the plurality of summing nodes 214. The processor 116 (shown in FIG. 1) may be configured to control which subsets of the second plurality of cells 206 are connected to each of the summing nodes 214. According to an embodiment, the plurality of summing nodes 214 includes four summing nodes: a first summing node 224, a second summing node 226, a third summing node 228, and a fourth summing node 230. A plurality of sets of receive switches 232 are used to selectively connect each of the second plurality of cells 206 to any one of the plurality of summing nodes 214.

Referring now to FIG. 2 and FIG. 3, as was described hereinabove, each of the distribution nodes 210 may carry signals of a different phase. Also, each of the transducer elements in the transmit aperture 154 may be connected to any one of the plurality of distribution nodes 210. As such, all of the transducer elements connected to a common distribution node will receive signals with generally the same phase. By determining which of the transducer elements are connected to each of the distribution nodes, it is possible for the processor 116 to steer the wavefront of the ultrasound beam in the desired direction.

Additionally, the signals from all of the transducer elements connected to a common summing node will be combined in the summing node according to an embodiment. After being combined in one of the summing nodes 214, the signals will travel to the beamformer 110 (shown in FIG. 1) to have the appropriate phase shift applied. Additional details about the handling of signals from the summing nodes will be described in more detail hereinafter.

Figure 4:
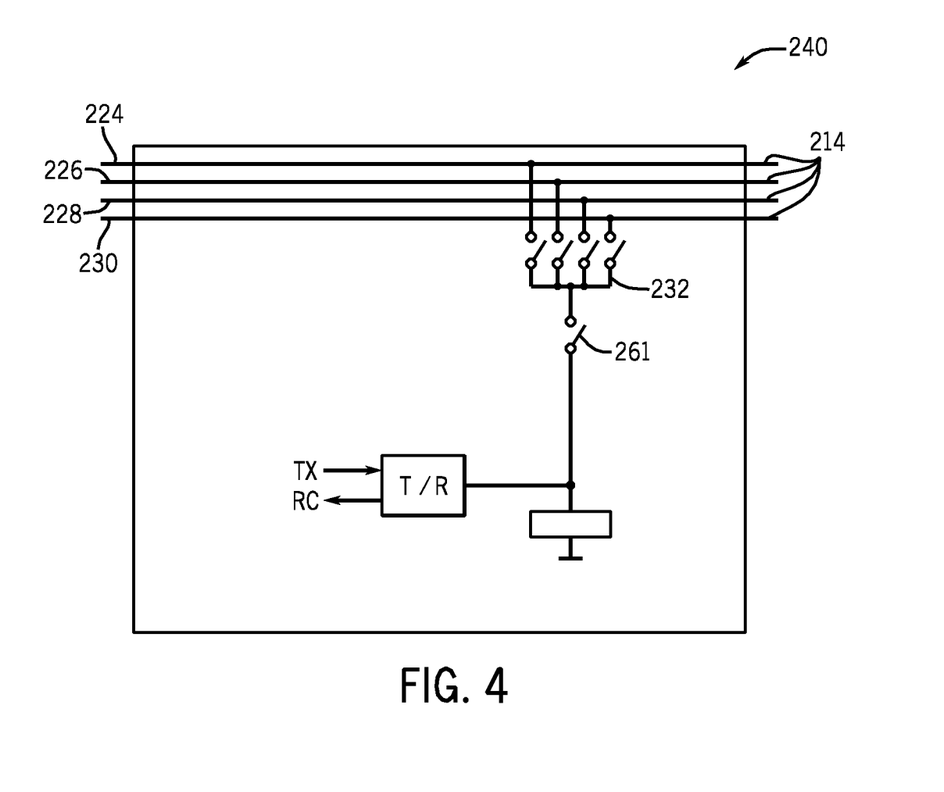
FIG. 4 is a schematic representation of a portion of an application-specific integrated circuit in accordance with an embodiment.

Referring to FIG. 4, a detailed schematic representation of a single cell 240 from the second plurality of cells 206 (shown in FIG. 3) of the ASIC 200 (shown in FIG. 3) is shown in accordance with an embodiment.

Referring to FIG. 4, a detailed schematic representation of a cell 240 from the second plurality of cells 206 (shown in FIG. 3) is shown in accordance with an embodiment. Each of the receive switches in the set of receive switches 232 may be selectively operated in order to connect a transducer element associated with cell 240 to one of four summing nodes: the first summing node 224, the second summing node 226, the third summing node 228, and the fourth summing node 230. Only one of the receive switches may actively connect the cell 240, and, therefore, the associated transducer element, to one of the plurality of summing nodes while the associated transducer element is actively receiving ultrasound signals. Signals from multiple transducer elements may be carried on each of the summing nodes. In this way, each of the plurality of summing nodes may combine ultrasound signals from multiple transducer elements. According to an embodiment, amplifiers connected to the summing nodes may be positioned in the console 123 (shown in FIG. 1). There may be a unique amplifier associated with each of the summing nodes 214. By combining signals on multiple summing nodes and handling the signal amplification in the console 123, the embodiment shown in FIG. 3 may more easily deliver the wide dynamic range necessary for imaging techniques like continuous-wave Doppler, even with a large number of transducer elements in a 2D transducer array. Additionally, by using distribution nodes 210 and summing nodes 214, it is possible to use fewer electrical lines to connect a two-dimensional transducer array to the console 123 (shown in FIG. 1). Using fewer electrical lines may allow for a simpler ultrasound probe, potentially saving both time and money during design and manufacturing processes.

Figure 5:
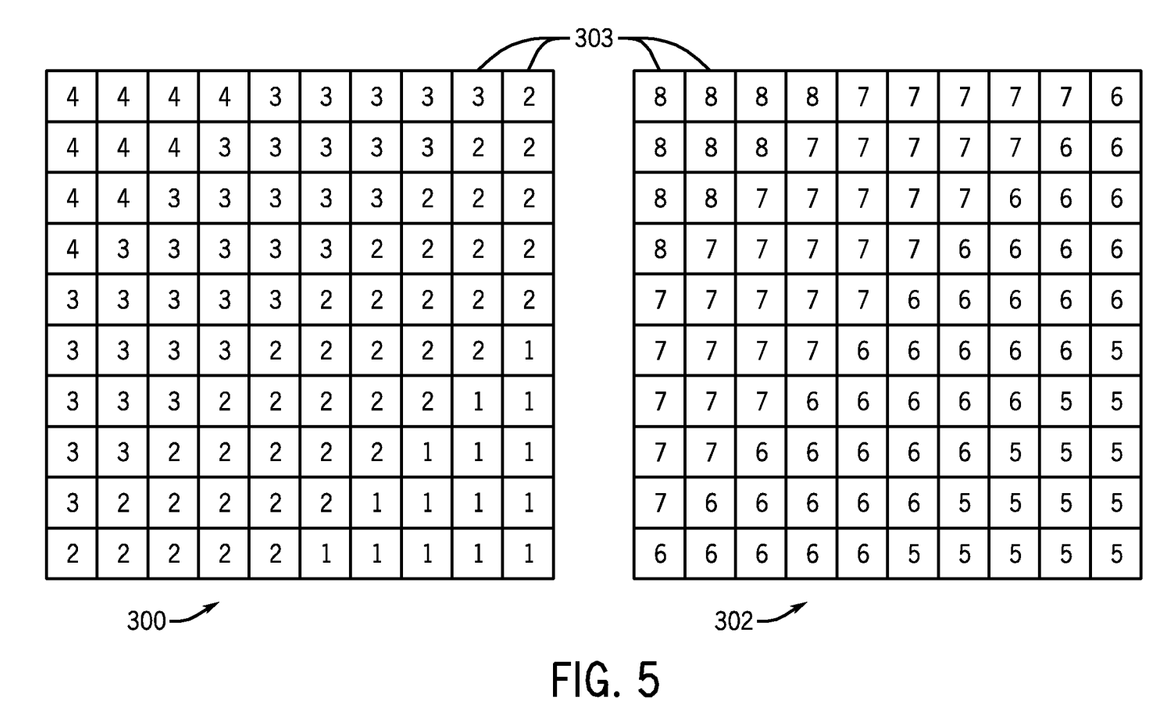
FIG. 5 is a schematic representation of a configuration for connecting transducer elements in accordance with an embodiment.

Referring to FIG. 5, a schematic representation of a configuration for connecting transducer elements to summing nodes and distribution nodes is shown in accordance with an embodiment. FIG. 5 includes both a transmit aperture 300 and a receive aperture 302. While the transmit aperture 300 and the receive aperture 302 are shown as separate from each other in FIG. 5, it should be appreciated that other embodiments may have transmit apertures and receive apertures of different configurations, and that the transmit aperture and the receive aperture may be adjacent to each other is some of these embodiments. The transmit aperture 300 and the receive aperture 302 each include a plurality of transducer elements 303. In FIG. 5, the number inside each of the transducer elements in the transmit aperture 300 represents the distribution node to which the transducer element is connected in accordance with an embodiment. For example, the transducer elements connected to the first distribution node are labeled with a "1", the transducer elements connected to the second distribution node are labeled with a "2", the transducer elements connected to the third distribution node are labeled with a "3", and the transducer elements connected to the fourth distribution node are labeled with a "4".

Likewise, the number inside each of the transducer elements in the receive aperture 302 represents the summing node to which the transducer element is connected in accordance with an embodiment. For example, the transducer elements connected to the first summing node are labeled with a "5", the transducer elements connected to the second summing node are labeled with a "6", the transducer elements connected to the third summing node are labeled with a "7", and the transducer elements connected to the fourth summing node are labeled with a "8".

According to an embodiment, the transducer elements in FIG. 5 may be grouped by phase. That is, all of the transducer elements in the transmit aperture 300 connected to a common distribution node may emit ultrasound signals with phases that are substantially the same. Additionally, signals from all of the transducer elements in the receive aperture 302 that are connected to a common summing node may be combined on the common summing node before a phase shift is applied to the signals. It should be appreciated that FIG. 5 represents one particular way the transducer elements may be connected to the nodes in accordance with one embodiment. The processor 116 (shown in FIG. 1) may change the connections of the sets of transmit switches and the sets of receive switches in order to change the focus of the transmit aperture or the receive aperture respectively. Each of the elements in the transmit aperture 300 may be selectively connected to any of the distribution nodes. Also, each of the transducer elements in the receive aperture 302 may be connected to any one of the summing nodes according to an embodiment. It should be appreciated that it would be possible to connect the transducer elements to the nodes in many additional configurations depending upon the desired focal points of the transmit aperture and the receive aperture.

Referring to both FIG. 3 and FIG. 4, according to an embodiment, there may be a phase shifter (not shown) located in the console 123 (shown in FIG. 1) connected to each of the distribution nodes 210. There may also be a phase shifter located in the console 123 connected to each of the summing nodes 214. With respect to the transmit aperture 154 (shown in FIG. 2), the phase shifters may be utilized to impart the proper phase shift to the signals carried by each of the distribution nodes 210. With respect to the receive aperture 156 (shown in FIG. 2), the phase shifters may be utilized to align the phases of the signals from each of the summing nodes so that the signals from each of the different summing nodes may be added together. For example, according to an exemplary embodiment with four summing nodes, the signals from the first summing node may be rotated by 45 degrees by a first phase shifter (not shown), the signal from the second summing node may be rotated by 135 degree by a second phase shifter (not shown), the signal from the third summing node may be rotated by 225 degrees by a third phase shifter (not shown), and the signal from the fourth summing node may be rotated by 315 degrees by a fourth phase shifter (not shown). It should be appreciated that the phase shifters may each rotate the signals by different amounts according to other embodiments.

Referring to FIG. 4, the cell 240 shown in FIG. 4 also includes a high-voltage switch 261. The high-voltage switch 261 may be controlled by the processor 116 (shown in FIG. 1). The high-voltage switch 261 may be used to isolate the set of receive switches 232 when the transducer array is operated in a pulsed-mode. For example, the processor 116 may selectively open the high-voltage switch 261 when the cell 240 is in a pulsed transmit mode (e.g. b-mode or color flow mode). The high-voltage switch 261 also serves to isolate the set of receive switches 232 from the high voltages present during the transmit phase of pulsed-mode operation. By using a high-voltage switch, such as the high-voltage switch 261, the set of receive switches 232 may be made much smaller since they do not need to withstand the voltages used during the transmit phase of pulsed-mode operation. During continuous-wave Doppler mode, the high-voltage switch 261 is closed to connect the transducer element to the set of receive switches 232. It should be appreciated that while the high-voltage switch 261 is shown as part of a cell in the receive aperture 208 (shown in FIG. 3), each of the first plurality of cells 204 (shown in FIG. 3) may also have similarly positioned high-voltage switches protecting each set of transmit switches 212 (shown in FIG. 3).

Still referring to FIG. 4, the switches 232 may be configured so that the transducer element (not shown) associated with the cell 240 may be connected to any one of the summing nodes (224, 226, 228, 230). According to an embodiment, the processor 116 (shown in FIG. 1) may control the configuration of the sets of receive switches in order to determine which specific transducer elements are connected to each summing node (224, 226, 228, 230). As discussed previously, there may be a cell, such as the cell 240, connected to each of the transducer elements. The transducer elements may be comprised of a material that changes its thickness in response to an electric current. For example, the transducer elements may be made from a piezoelectric material or an electrostrictive material. Alternatively, the transducer elements may be made as a capacitive micromachined ultrasound transducer (cMUT). According to an embodiment, a plurality of cells, such as the cells that are part of the ASIC 200 (shown in FIG. 3) may be immediately behind a layer of transducer elements or they may be located anywhere inside the ultrasound probe 106 (shown in FIG. 1). The processor 116 may then calculate the required state of each of the sets of transmit switches 212 (shown in FIG. 3) connecting the transducer elements in the transmit aperture to the distribution nodes 210 (shown in FIG. 3). Based on the number of distribution nodes used for the transmit aperture and the number of summing nodes used for the receive aperture, the processor 116 may then determine which transducer elements should be connected to a common node. For example, the processor 116 may group the transducer elements into four groups as in the previously described exemplary embodiment.

Figure 6:
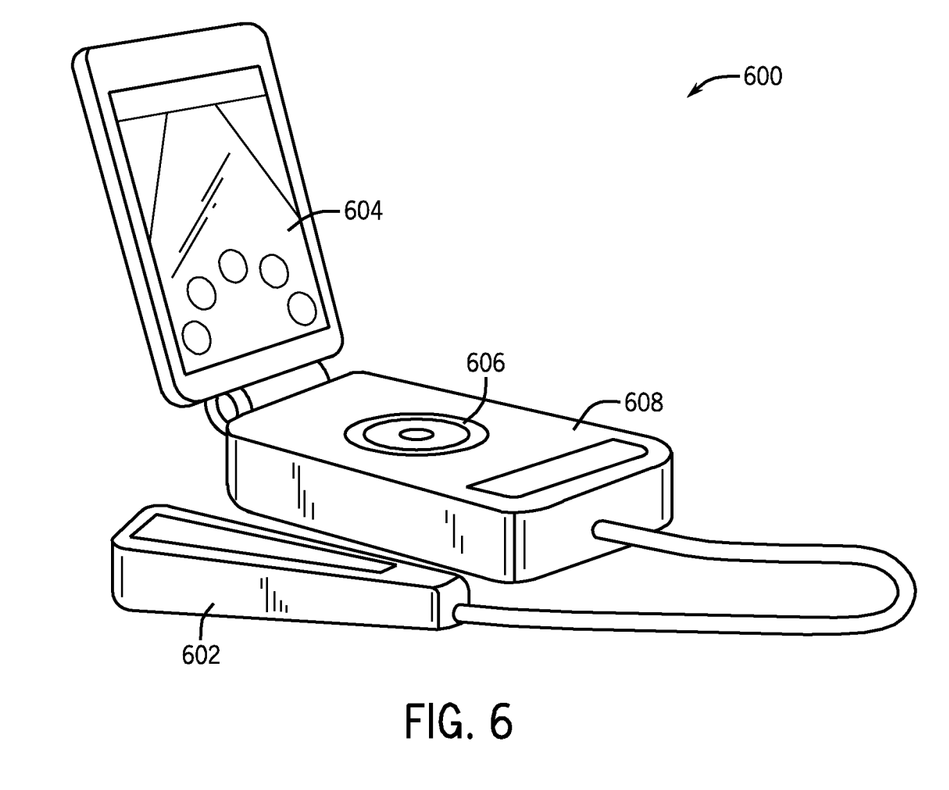
FIG. 6 is a schematic representation of a hand-held ultrasound imaging system in accordance with an embodiment.

Referring now to FIG. 6, a hand-held ultrasound imaging system is shown in accordance with an embodiment. The hand-held ultrasound imaging system 600 includes an ultrasound probe 602, a display 604, and a user interface 606. The user interface 606 may comprise a touch wheel and/or other buttons. Embodiments may also use soft keys and/or a touch screen located on the display 604 as part of the user interface. The ultrasound imaging system 600 also includes a housing 608 that encases additional components. According to an embodiment, the hand-held ultrasound imaging system 600 may include all of the elements shown as within the console 123 (shown in FIG. 1) of FIG. 1 within the housing 608. The probe, 602, may likewise comprise a 2D transducer array similar to the one shown in FIG. 3. It should be appreciated by those skilled in the art that other embodiments may include a housing with a substantially different shape.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An ultrasound probe comprising:
    a 2D transducer array comprising a plurality of transducer elements, the plurality of transducer elements organized to form a transmit aperture and a receive aperture, wherein the transmit aperture and the receive aperture do not overlap with each other;
    a plurality of summing nodes; and
    a plurality of sets of receive switches, each set of receive switches comprising a plurality of receive switches, each set of receive switches being associated with a different one of the plurality of transducer elements in the receive aperture, each set of receive switches configured to selectively connect the associated transducer element to any one of the plurality of summing nodes without an amplifier electrically connected between the associated transducer element and the one of the plurality of summing nodes when in a continuous-wave Doppler mode.

2. The ultrasound probe of claim 1, wherein the plurality of transducer elements in the receive aperture are connected to the plurality of summing nodes via the plurality of sets of receive switches based on a phase of a receive signal from each of the plurality of transducer elements.

3. The ultrasound probe of claim 1, wherein a subset of the plurality of transducer elements in the receive aperture is connected to a first of the plurality of summing nodes.

4. The ultrasound probe of claim 3, wherein receive signals from the subset of the plurality of transducer elements in the receive aperture have a phase that is the same.

5. The ultrasound probe of claim 1, wherein the plurality of transducer elements are arranged in a two-dimensional array.

6. The ultrasound probe of claim 1, wherein the plurality of summing nodes comprises four summing nodes.

7. An ultrasound imaging system comprising:
    an ultrasound probe comprising:
        a 2D transducer array comprising a plurality of transducer elements, the plurality of transducer elements organized to form a transmit aperture and a receive aperture, wherein the transmit aperture and the receive aperture do not overlap with each other;
        a plurality of summing nodes;
        a plurality of sets of receive switches, each set of receive switches comprising a plurality of receive switches, each set of receive switches being associated with a different one of the transducer elements in the receive aperture, each set of receive switches configured to connect the associated transducer element to any one of the plurality of summing nodes without an amplifier electrically connected between the associated transducer element and the one of the plurality of summing nodes; and
    a console comprising:
        a processor connected to the ultrasound probe, the processor configured to control the plurality of sets of receive switches in order to selectively connect a subset of the plurality of transducer elements in the receive aperture to one of the plurality of summing nodes in a continuous-wave Doppler mode, and a plurality of amplifiers, where each of the plurality of amplifiers is connected to one of the plurality of summing nodes.

8. The ultrasound imaging system of claim 7, wherein the processor is further configured to control the plurality of sets of receive switches in order to connect another subset of the plurality of transducer elements in the receive aperture to another of the plurality of summing nodes.

9. The ultrasound imaging system of claim 7, further comprising a plurality of distribution nodes connected to the processor.

10. The ultrasound imaging system of claim 9, further comprising a plurality of sets of transmit switches, each of the sets of transmit switches associated with a different one of the transducer elements in the transmit aperture, each set of transmit switches configured to selectively connect the associated transducer element to any one of the plurality of distribution nodes.

11. The ultrasound imaging system of claim 10, wherein the processor is further configured to control the plurality of sets of transmit switches to connect a subset of transducer elements in the transmit aperture to one of the distribution nodes.

12. The ultrasound imaging system of claim 11, wherein the processor is further configured to steer the receive aperture by controlling which of the transducer elements in the receive aperture are connected to each of the summing nodes via the sets of receive switches.

13. The ultrasound imaging system of claim 12, wherein the processor is further configured to steer the transmit aperture by controlling which of the transducer elements in the transmit aperture are connected to each of the distribution nodes via the sets of transmit switches.

14. The ultrasound imaging system of claim 11, wherein the processor is further configured to connect each of the plurality of transducer elements to either a summing node or a distribution node during the continuous-wave Doppler mode.

15. The ultrasound imaging system of claim 7, further comprising a housing including the processor and a user interface, the housing comprising a size and weight configured for hand-held use.

16. The ultrasound imaging system of claim 10, further comprising a plurality of transmitters, where each of the plurality of transmitters is connected to one of the plurality of distribution nodes.

17. An ultrasound probe comprising:

a 2D transducer array comprising a plurality of transducer elements arranged in an array, the plurality of transducer elements organized to form a transmit aperture and a receive aperture, wherein the transmit aperture and the receive aperture do not overlap with each other;

a plurality of summing nodes;

a first set of receive switches associated with a first transducer element in the receive aperture, the first set of receive switches comprising a first plurality of receive switches, wherein the first set of receive switches is configured to selectively connect the first transducer element to any one of the plurality of summing nodes;

a second set of receive switches associated with a second transducer element in the receive aperture, the second set of receive switches comprising a second plurality of receive switches, wherein the second set of receive switches is configured to selectively connect the second transducer element to any one of the plurality of summing nodes; and wherein the first set of receive switches and the second set of receive switches are collectively configured to connect both the first transducer element and the second transducer element to the same one of the plurality of summing nodes without an amplifier electrically connected between the first and second transducer elements and the one of the plurality of summing nodes.

18. The ultrasound probe of claim 17, further comprising:

a plurality of distribution nodes;

a first set of transmit switches associated with a third transducer element in the transmit aperture, the first set of transmit switches comprising a first plurality of transmit switches, wherein the first set of transmit switches is configured to selectively connect the third transducer element to anyone of the plurality of distribution nodes;

a second set of transmit switches associated with a fourth transducer element in the transmit aperture, the second set of transmit switches comprising a second plurality of transmit switches, wherein the second set of transmit switches is configured to selectively connect the fourth transducer element to any one of the plurality of distribution nodes; and wherein the first set of transmit switches and the second set of transmit switches are collectively configured to connect both the third transducer element and the fourth transducer element to the same one of the plurality of distribution nodes.

19. A method of ultrasound imaging with an ultrasound probe including a 2D transducer array with a transmit aperture that does not overlap a receive aperture, the method comprising:

connecting a plurality of transducer elements in the receive aperture to a first summing node;

combining a first plurality of signals from the plurality of transducer elements in the first summing node;

displaying a first image based on the first plurality of signals;

connecting the plurality of transducer elements in the receive aperture to a second summing node after said combining the first plurality of signals in the first summing node;

combining a second plurality of signals from the plurality of transducer elements in the second summing node; and displaying a second image based on the second plurality of signals.

20. The method of claim 19, further comprising connecting the plurality of transducer elements in the receive aperture to a third summing node, combining a third plurality of signals from the plurality of transducer elements in the third summing node, and displaying a third image based on the third plurality of signals.

21. The method of claim 19, further comprising amplifying the first plurality of signals in an amplifier located outside of the probe after said combining the first plurality of signals.

22. The method of claim 21, further comprising amplifying the second plurality of signals in a second amplifier located outside of the probe after said combining the second plurality of signals.

23. The method of claim 21, wherein the amplifier is located in a console of an ultrasound imaging system.

\* \* \* \* \*